US011623277B2

(12) United States Patent
Molina Jordá

(10) Patent No.: US 11,623,277 B2
(45) Date of Patent: Apr. 11, 2023

(54) OPEN-PORE FOAM MATERIALS WITH GUEST PHASES, PROCEDURE FOR THE PREPARATION OF THESE MATERIALS AND USES THEREOF

(71) Applicant: Universidad de Alicante, Alicante (ES)

(72) Inventor: José Miguel Molina Jordá, Alicante (ES)

(73) Assignee: Universidad de Alicante, Alicante (ES)

( * ) Notice: Subject to any disclaimer, the term of this patent is extended or adjusted under 35 U.S.C. 154(b) by 97 days.

(21) Appl. No.: 16/628,703

(22) PCT Filed: Jul. 3, 2018

(86) PCT No.: PCT/ES2018/070474
§ 371 (c)(1),
(2) Date: Jan. 6, 2020

(87) PCT Pub. No.: WO2019/008208
PCT Pub. Date: Jan. 10, 2019

(65) Prior Publication Data
US 2020/0189002 A1      Jun. 18, 2020

(30) Foreign Application Priority Data

Jul. 5, 2017   (ES) ............................... ES201730890

(51) Int. Cl.
*B22F 3/26*       (2006.01)
*A61K 47/02*      (2006.01)
(Continued)

(52) U.S. Cl.
CPC ............... *B22F 3/26* (2013.01); *A61K 47/02* (2013.01); *A61K 47/32* (2013.01); *A61K 47/34* (2013.01);
(Continued)

(58) Field of Classification Search
CPC ............ C08J 9/365; Y10T 428/249986; Y10T 428/249987; Y10T 428/249954;
(Continued)

(56) References Cited

U.S. PATENT DOCUMENTS

| 4,027,476 A | * | 6/1977 | Schmidt | .................... B01J 35/02 |
| | | | | 60/218 |
| 5,716,997 A | * | 2/1998 | Toyosawa | ............. C08L 53/025 |
| | | | | 521/64 |

(Continued)

FOREIGN PATENT DOCUMENTS

| WO | WO 2009/091292 | 7/2009 |
| WO | WO 2014/210608 | 12/2014 |

(Continued)

OTHER PUBLICATIONS

Informe de Busqueda Internacional y Opinion Escrita [International Search Report and the Written Opinion] dated Nov. 15, 2018 From the International Searching Authority Re. Application No. PCTES2018/070474 and Its Translation of Search Report Into English. (13 Pages).

(Continued)

*Primary Examiner* — Hai Vo

(57) ABSTRACT

The present invention relates to a foam material comprising:—a structural matrix (1),—at least one guest phase (2), and—a fluid, the material being characterised in that the structural matrix (1) comprises a plurality of interconnected pores (3), the one or more guest phases (2) are accommodated inside at least one pore (3) of the structural matrix (1) and the fluid is accommodated inside the pores (3). The present invention further relates to the process for preparing the foam material according to the present invention and to the various uses of the foam material according to the present invention.

8 Claims, 5 Drawing Sheets

(51) Int. Cl.
| | |
|---|---|
| A61K 47/32 | (2006.01) |
| A61K 47/34 | (2017.01) |
| A61K 47/38 | (2006.01) |
| B01J 20/28 | (2006.01) |
| B01J 35/04 | (2006.01) |
| B22F 3/02 | (2006.01) |
| B29C 44/02 | (2006.01) |
| C04B 41/00 | (2006.01) |
| C04B 41/45 | (2006.01) |
| C04B 41/50 | (2006.01) |
| C08J 9/36 | (2006.01) |
| H01M 4/04 | (2006.01) |
| B22F 3/24 | (2006.01) |
| B29K 509/02 | (2006.01) |

(52) U.S. Cl.
CPC ......... *A61K 47/38* (2013.01); *B01J 20/28045* (2013.01); *B01J 35/04* (2013.01); *B22F 3/02* (2013.01); *B29C 44/02* (2013.01); *C04B 41/009* (2013.01); *C04B 41/4545* (2013.01); *C04B 41/5059* (2013.01); *C08J 9/365* (2013.01); *H01M 4/0416* (2013.01); *B22F 2003/247* (2013.01); *B29K 2509/02* (2013.01); *Y10T 428/249954* (2015.04); *Y10T 428/249955* (2015.04); *Y10T 428/249987* (2015.04)

(58) Field of Classification Search
CPC .......... Y10T 428/249955; C04B 35/52; C04B 38/0058; C04B 38/045; C04B 41/009; C04B 41/4545; C04B 41/5059; C22C 1/0416; C22C 1/0475; C22C 1/08; C22C 1/101; C22C 1/1036; C22C 2001/081; C22C 2001/1021; C22C 2001/1073; C22C 32/0063; H01M 4/0416; Y02E 60/10

See application file for complete search history.

(56) References Cited

U.S. PATENT DOCUMENTS

2011/0283873 A1* 11/2011 Wadley .................... B32B 5/02
    89/36.02
2016/0208175 A1* 7/2016 Groppi .................... B01J 8/067

FOREIGN PATENT DOCUMENTS

WO  WO-2015033266 A1 *  3/2015  .......... B01J 19/2485
WO  WO 2019/008208         1/2019

OTHER PUBLICATIONS

Gentile et al. "Influence of Parathyroid Hormone-Loaded PLGA Nanoparticles in Porous Scaffolds for Bone Regeneration", International Journal of Molecular Sciences, 16(9): 20492-20510, Aug. 28, 2015.

Molina Jorda "Mesophase Pitch-Derived Graphite Foams With Selective Distribution of TiC Nanoparticles for Catalytic Applications", Carbon, 103: 5-8, Pubhshed Online Feb. 26, 2016.

Scott et al. "A Simple Water-Based Synthesis of Au Nanoparticle/PDMS Composites for Water Purification and Targeted Drug Release", Macromolecular Chemistry and Physics, 211(15): 1640-1647, Aug. 2, 2010.

* cited by examiner

FIG. 4
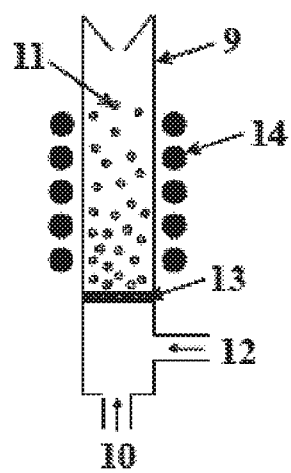
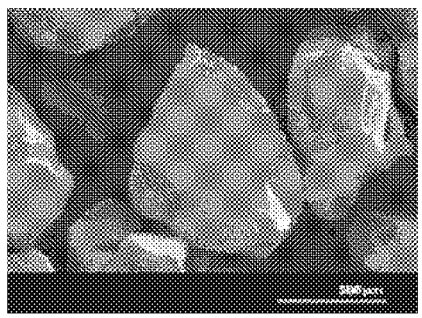
FIG. 5(a)
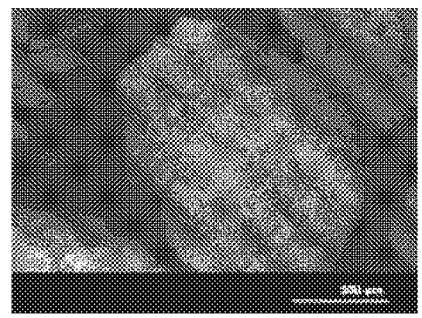
FIG. 5(b)
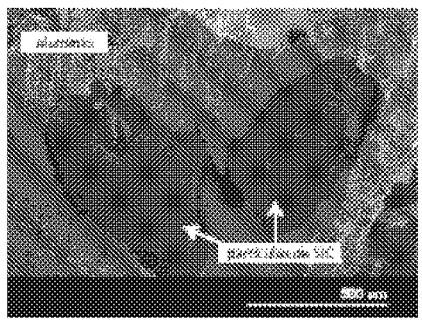
FIG. 5(c)
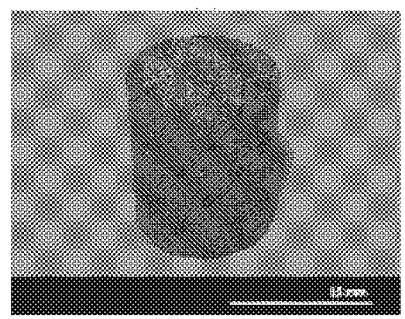
FIG. 5(d)

OPEN-PORE FOAM MATERIALS WITH GUEST PHASES, PROCEDURE FOR THE PREPARATION OF THESE MATERIALS AND USES THEREOF

RELATED APPLICATIONS

This application is a National Phase of PCT Patent Application No. PCT/ES2018/070474 having International filing date of Jul. 3, 2018, which claims the benefit of priority of Spanish Patent Application No. P201730890 filed on Jul. 5, 2017. The contents of the above applications are all incorporated by reference as if fully set forth herein in their entirety.

FIELD AND BACKGROUND OF THE INVENTION

The invention falls within the field of foam materials and in particular relates to a foam material with interconnected pores containing inside the pores thereof at least one guest phase, which provides the foam material with specific functional features.

Foam materials with interconnected pores have been known for a long time. The first advances were reported in this line during the 1960s and they explain processes for manufacturing metal foams.

Since then, many methods for manufacturing foam materials made of metals, ceramics and polymers have been developed. The wide range of fabrication methods can be classified into four groups, depending on the state of aggregation of the precursor material of the foam (Banhart, J., 2001. Manufacture, characterisation and application of cellular metals and metal foams. Prog. Mater. Sci. 46, 559-632).

The methods are as follows:

Liquid state processing: The precursor material is in a liquid state. The most important synthesis routes of this type of processing are the following:
 a) Direct injection of gas into the liquid.
 b) Introduction of gas-generating agents.
 c) Solidification from solid-gas eutectics ("gasars").
 d) Melting of powder mixtures with gas-generating agents.
 e) Lost-foam casting with polymeric foams.
 f) Infiltration of martyr preforms.
 g) Metal atomisation ("Osprey process").

Solid state processing: The precursor material is in a solid state. The following routes are the most important ones:
 h) Partial sintering of particles and fibres.
 i) Sintering with gas occlusion.
 j) Foaming of sludge formed by powders, gas-generating agents and additives.
 k) Pressurisation and sintering of powders around martyrs.
 i) Sintering of hollow spheres.
 m) Sintering of powders and binders.
 n) Reactive sintering of multicomponent systems.

Vapour state processing:
 o) Deposition from the vapour phase on polymeric foams.

Dissolution state processing:
 p) Electrochemical deposition on polymeric foams.

Despite the wide range of production methods that these four groups generate, in reality there are only two different strategies for generating porosity (Körner C, Singer RF., 2001. Processing of metal foams - challenges and opportunities. Adv. Eng. Mater. 2, 159-165.):

Self-formation: In it, the porosity is formed through a self-evolution process according to physical principles. The nature of the pores is stochastic and the structure of the cells is created to minimise the free energy of the system, including external forces and boundary conditions. The cell walls need to be stabilised by means of the addition of additives, since the majority of pure materials (such as metals) do not tend to foam due to the high surface tension and low viscosity thereof. The geometry of the cells can vary from spherical to polyhedral and, in general, they are closed cells, although small cracks frequently appear which connect them to each other. Among the self-formation methods from the previous list, the following stand out: a, b, c, d, g, i, j.

Pre-design: The structure is created by using moulds which determine the pores. This strategy enables the formation of a wide spectrum of cell geometries and sizes, as well as relative densities. The porosity thus generated is more homogeneous than that of self-formation, and for this reason the dispersion in the properties of these materials is lesser. In this case, it is not necessary to use additives, since the cell walls stay stabilised by the walls of the mould. By means of this strategy, close-pore (or not interconnected) and open-pore (or interconnected) foams can be manufactured, depending on whether the mould is part of the final material or is removed, respectively. Among the pre-design methods from the previous list, the following stand out: e, f, h, k, I, m, n, o, p.

The foams manufactured until now following one of the previous methods have shown to be useful in many applications, among which it is worth noting the following: heat exchange, filtration, silencing, impact absorption, noise absorption, catalyst support, biomedical implants, etc.

Of all the methods developed, the one which enables the best control over the obtained material is the method of infiltrating martyr preforms (method f), also known as the replication method.

With this method, metal, ceramic and polymeric foams with open (or interconnected) pores are manufactured by means of filling by infiltration with the molten material of the foam (or a precursor thereof) the open pores of a martyr preform which is subsequently removed. In the most common version this method consists of the following steps:
 i) Selection of a sacrificial material that is finely divided (particles or fibres) such that it fulfils the following requirements:
  a. it must be refractory with respect to the infiltrating liquid (having a higher melting/softening point than it);
  b. it must be able to be easily removed by dissolution or controlled chemical reaction after the infiltration;
  c. it must be chemically compatible with the material that will make up the foam in all the steps of the process, including the infiltration and the removal thereof (it must not cause degradation or corrosion in the foam material).
 ii) Manufacture of a porous preform with the sacrificial material by means of some consolidation method such as compacting (this step may require the application of pressure, or pressure and vibrations, or also a heating step) or sintering.
 iii) Introduction of the preform into an infiltration chamber, wherein a vacuum is applied and then the temperature is raised to a temperature above that of melting/softening temperature of the infiltrating liquid.

iv) Infiltration of the preform with the infiltrating liquid by means of the application or not of mechanical or gaseous pressure so that the penetration of the liquid in the pores of the preform is produced.

v) Solidification of the matrix and removal of the sacrificial material that makes up the original preform by means of dissolution or controlled chemical reaction, giving rise to a foam with interconnected pores.

This replication method was used extensively with sacrificial particles made up of sodium chloride (NaCl), as described in the patents containing the original ideas of this method, U.S. Pat. Nos. 3,210,166 and 3,236,706. Many metal, ceramic and polymeric foam materials were made changing therein the porosity (in the interval 50%-90%), the shape of the pores (using salt crystals with different shapes) and pore sizes (in the interval 0.5 μm-6 mm) (Banhart, J., 2001. Manufacture, characterisation and application of cellular metals and metal foams. Prog. Mater. Sci. 46, 559-632); (Despois, J. F., Conde, Y., Marchi, C. S., Mortensen, A., 2004. Tensile behavior of replicated aluminium foams. Adv. Eng. Mater. 6, 444-447); (San Marchi, C, Mortensen, A., 2001. Deformation of open-cell aluminum foam. Acta Mater. 49, 3959-3969.); (San Marchi, C, Despois, J. F., Mortensen, A., 2004. Uniaxial deformation of open-cell aluminum foam: The role of infernal damage. Acta Mater. 52, 2895-2902); Goodall, R., Marmottant, A., Salvo, L, Mortensen, A., 2007. Spherical pore replicated microcellular aluminium: Processing and influence on properties. Mater. Sci. Eng. A 465, 124-135.); (Prieto, R., Louis, E., Molina, J. M., 2012. Fabrication of mesophase pitch-derived open-pore carbon foams by replication processing. Carbon N. Y. 50, 1904-1912.)

The advantages of this method with respect to others lies in the fact that the pores in the foam material replicate the features of the material making up the preform and which acts as a sacrificial material. In this manner, the pores of the foam material possess the features of size, distribution of sizes and shapes of the particles or fibres of the original preform made up of the sacrificial material (Gaillard, C, Despois, J. F., Mortensen, A., 2004. Processing of NaCl powders of controlled size and shape for the microstructural tailoring of aluminium foams. Mater. Sci. Eng. A 374, 250-262). For these reasons, the replication method has become one of the most versatile for manufacturing foams of all kinds: metal, polymeric and ceramic (made of carbon, graphite, etc.).

The replication method requires the suitable choice of the nature of the sacrificial material, with the object of fulfilling the condition of being more refractory than the infiltrating liquid and chemically compatible with it during all the steps of the process. The sodium chloride (NaCl) salt has an average melting point of 801° C. and for this reason the manufacturing of foams is limited to infiltrating liquids with a melting point below 801° C. Thus, with preforms manufactured by compacting NaCl particles, foams made of Al, Mg, Sn, Pb, etc. or alloys thereof can be manufactured without difficulty by means of infiltration with these metals and subsequent dissolution in aqueous solutions. However, by using NaCl particles, foams made of Ag or Cu cannot be manufactured, for example, since these metals have melting points higher than 801° C. For these metals, it is necessary to use other divided materials with a higher melting point, such as particles or fibres made of carbon or graphite, which can be removed after the infiltration with these metals by means of combustion in air, or salts of the type disclosed in patent U.S. Pat. No. 3,210,166, which can be removed by means of dissolution in aqueous solutions. Additionally, other salts can be used such as $K_2CO_3$ (Conde, Y., Despois, J. F., Goodall, R., Marmottant, A., Salvo, L, Marchi, C. S., Mortensen, A., 2006. Replication processing of highly porous materials. Adv. Eng. Mater. 8, 795-803), $TiH_2$ or $CaCO_3$ (Lefebvre, B. L., Banhart, J., Dunand, D. C., 2008. Porous metals and metallic foams: current status and recent developments 10, 775-787), which can be removed by thermal decomposition ($TiH_2$) or by dissolution or thermal decomposition ($K_2CO_3$ and $CaCO_3$), strontium fluorides ($SrF_2$) or barium ($BaF_2$), able to be removed by dissolution, or $NaAlO_2$, $Al_2(SO_4)_3$, BaS, $K_2SO_4$ or $Na_2S$ (EP2118328), able to be removed by dissolution. $MgSO_4$ can also be used (Diologent, F., Combaz, E., Laporte, V., Goodall, R., Weber, L, Duc, F., Mortensen, A., 2009. Processing of Ag—Cu alloy foam by the replication process. Ser. Mater. 61, 351-354.), since it is able to be removed by dissolution or by thermal decomposition, and $SiO_2$, able to be removed by dissolution in an acidic solution (Castrodeza, E. M., Mapelli, C, Vedani, M., Arnaboldi, S., Bassani, P., Tuissi, A., 2009. Processing of shape memory CuZnAl open-cell foam by molten metal infiltration. J. Mater. Eng. Perform. 18, 484-489).

One of the most notable disadvantages of the replication method comes from the limitation in the size and shape of the available salt crystals, as well as the fact that the largest crystals (>0.5 mm) cannot be compacted in the same manner as the smaller ones, given the usual different geometry thereof. Furthermore, for the larger crystals, the dissolution times increase considerably and, with this, the processing costs and the risk that the foam may be affected by corrosion due to prolonged contact with the dissolving liquid. For this reason, processing pathways have been developed which substitute the sodium chloride (NaCl) particles with particles formed starting from a paste made up of a mixture of NaCl, flour and water (EP 2118328); (U.S. Pat. No. 8,151,860); (Goodall, R., Mortensen, A., 2007. Microcellular aluminium—child's play! Adv. Eng. Mater. 9, 951-954.).

This paste is moulded in the form of small masses with the desired geometry which, when arranged suitably, form a preform. Afterwards, this preform is subjected to a thermal treatment wherein the carbohydrates of the flour pyrolyse and the majority of the carbon present is removed by reaction with oxygen. This leaves a preform made of salt containing many small pores. The most evident advantage in the use of these preforms is that they can be dissolved in an order of magnitude less time with respect to if they are made with salt crystals of the same size.

The foams manufactured by replication possess a wide spectrum of applications, given the fact that they can be designed depending on specific needs. Some of these have proved to be suitable as catalyst support in gas or liquid-phase reactions, since the presence of interconnected pores enables the passage of fluid through them and for this reason they can be used in continuous reactors. However, the use thereof has not become widespread for this application due to the fact that the foams that are intended to be used as catalyst support must meet two requirements, which are often contradictory:

i) the foams must have a high specific surface, such that they enable a high dispersion of the catalytically-active phase;

ii) the pore size must not be too small in order to prevent the pressure drop of the fluid passing through it from being too large.

Furthermore, the foams intended to be used for these aims must have another property: the thermal conductivity thereof must be as high as possible in order to favour the heat transport from or to the outside of the catalytic reactor (for endothermic or exothermic reactions, respectively).

Some of the more recent developments in foams seem to combine the properties of good permeability to the passage of fluids with high thermal conductivity, and also enable the specific surface of the foams to be increased by means of the incorporation of nanoparticles which act as catalysts or support for catalysts and are anchored to the surface of the pores of the foams (Molina-Jordá, J. M., 2016. Mesophase pitch-derived graphite foams with selective distribution of TiC nanoparticles for catalytic applications. Carbon N. Y. 103, 5-8). In any case, the specific surface of these foam materials (of the order of 1 m$^2$/g) is still too low to use these materials in some catalytic applications.

Additionally, recently, the use of foams with interconnected pores has been proposed in medical applications for implantology, since it is potentially possible to make living tissue grow inside the cavities and thereby diminish the risk of encystment which can be produced when a solid implant is used. However, using materials with a specific surface that is so relatively high like foams (with respect to solid materials) makes it more complicated to ensure the complete sterilisation thereof prior to the application. For this reason, new, special protocols must be designed for actuating when implanting these materials in living beings.

For some applications in electronics, it would be convenient to use foams with certain magnetic properties. However, the use thereof is restricted since until now only the manufacture of foams made of iron or cobalt has been proposed as a solution, the manufacture of which is very complicated and expensive due to the high melting points of these materials. Furthermore, the higher density thereof limits the use of these materials for electronic systems in ground or aeronautical transportation means.

Therefore, there is a need to develop new foam materials that are easily manufactured and that have improved properties, the functional features of which is not limited by the material the foam material is made of, or by the size, shape and size distribution of the pores thereof.

SUMMARY OF THE INVENTION

The present invention, in a first aspect, relates to a foam material (hereinafter referred to as the foam material of the present invention) comprising:
  a structural matrix,
  at least one guest phase and
  a fluid,
characterised in that the structural matrix comprises a plurality of interconnected pores, the guest phase is accommodated inside at least one pore of the structural matrix and the fluid is accommodated inside the pores.

In one particular embodiment, the guest phases are accommodated inside the pore of the structural matrix, without maintaining any bond with the latter, so that between the walls of the pores of the foam material and the surface of the guest phases there is a gauge of space that is occupied by the fluid.

In one particular embodiment, the structural matrix of the foam material of the present invention is made up of a material that is metal, polymeric, ceramic or mixtures thereof.

In an even more particular embodiment, if the structural matrix of the foam material of the present invention is metal, the material of the structural matrix is selected from among a pure metal, metal alloys and mixtures thereof. In an even more particular embodiment, the pure metal is selected from among tin, lead, magnesium, aluminium, silver, copper and titanium, among others, metal alloys that can contain them and mixtures thereof.

In another even more particular embodiment, if the structural matrix of the foam material of the present invention is ceramic, the material of the structural matrix is selected from among carbon, graphite, silicon, silicon carbide, alumina and zeolites, among others, and mixtures thereof.

In another even more particular embodiment, if the structural matrix of the foam material of the present invention is polymeric, the material of the structural matrix is selected from among nitrocellulose, vulcanised rubber, nylon, vinyl polychloride, polystyrene, polyethylene, poly(methyl methacrylate), polypropylene, polyethylene terephthalate and polyurethane, among others, and mixtures thereof.

In another particular embodiment, the structural matrix of the foam material of the present invention is made up of more than one material with different natures, such as a mixture of metals, mixture of ceramics, mixture of polymers and/or a combination of all of these.

In one particular embodiment, the guest phase of the foam material of the present invention is a functional material.

In the present invention, functional material is understood as any material which confers a certain function, such as, for example, a function that is adsorbent, absorbent (for impacts or radiation), catalytic, magnetic, supporting, catalyst-supporting, for releasing chemical and pharmaceutical substances, an electrode function, etc.

In an even more particular embodiment, the functional material of the guest phase of the foam material of the present invention is selected from among materials that are adsorbent, catalytic, magnetic, catalyst-supporting, for releasing chemical and pharmaceutical substances, electrode materials, radiation-absorbing materials, dielectric materials and any other type of material which confers a certain function to the foam material of the present invention.

More particularly, the functional material is selected from among: carbon, actived carbon, graphite, alumina ($Al_2O_3$), activated alumina ($Al_2O_3$), silicon carbide (SiC), silicon (Si), activated silicon carbide (SiC), titanium carbide (TiC), activated titanium carbide (TiC), aluminium nitride (AlN), activated aluminium nitride (AlN), cerium ($CeO_2$), activated cerium ($CeO_2$), titania ($TiO_2$), activated titania ($TiO_2$), zeolites, metal-organic frameworks ($MOF_s$), platinum (Pt), rhodium (Rh), palladium (Pd), iron, cobalt, nickel and metal alloys containing them, iron oxides ($Fe_xO_y$), cobalt oxides ($Co_xO_y$), and nickel oxides ($Ni_xO_y$).

In another particular embodiment, the fluid accommodated inside the pores of the foam material of the present invention is a gas or a liquid.

In a more particular embodiment, the fluid accommodated inside the pores of the foam material of the present invention is an inert or reactive gas, in a pure state or in the form of a mixture of gases, with a pressure comprised between 0.01 mbar and 10 bar.

In another more particular embodiment, the fluid accommodated inside the pores of the foam material of the present invention is a liquid. More particularly, it is water, wastewater, contaminated aqueous solutions, ethanol, physiological serum, physiological fluid, etc.

More particularly, the fluid surrounds the entirety or a large portion of the one or more guest phases in the pore, such that the fluid can circulate through the inside of the foam material, since the latter has interconnected porosity, and be renewed if a pressure gradient prevails in the ends thereof.

In a particular embodiment, the foam material of the present invention comprises a guest phase which is accommodated in the entirety of the pores.

In a particular embodiment, the foam material of the present invention comprises a guest phase which is accommodated in a portion of the pores, leaving the rest of the cavities free of guest phases and completely occupied by the fluid.

In another particular embodiment, the foam material of the present invention comprises more than one guest phase which are accommodated in the entirety of the pores.

In another particular embodiment, the foam material of the present invention comprises more than one guest phase which are accommodated in a portion of the pores, leaving the rest of the cavities free of guest phases and completely occupied by the fluid.

In a second aspect, the present invention relates to a method for preparing a foam material of the present invention comprising the following steps:

a) coating of the one or more guest phases which were previously divided into particles or fibres, with at least one sacrificial material, b) compaction of the one or more coated guest phases obtained in step a) until a porous preform is formed, c) infiltration of the porous preform of step b), with a precursor liquid of the structural matrix, d) solidification of the liquid precursor of step c) and machining, e) removal pf the sacrificial material coating the guest phase.

In a particular embodiment, the sacrificial material of step a) is a salt selected from among halides, carbonates, fluorides, aluminates, sulphates and silicates.

In another particular embodiment, step a) comprises the use of two or more different sacrificial materials.

In the present invention, step a) of coating the one or more previously divided guest phases is performed by means of any conventional coating technique, such as, for example: magnetically-assisted impact coating, forced spray precipitation, impregnation, vapour phase deposition, coprecipitation from dissolution, fluidised bed spray coating, ball mill assisted coating, hot mixing and coating by spheroidising the feeding material.

In the present invention, step a) of coating the one or more previously divided guest phases enables continuous coatings to be created, with the aim of creating materials wherein the guest phase does not maintain any bond with the structural matrix.

In the present invention, step b) of compacting the one or more coated guest phases obtained in step a) until a porous preform is formed is performed by means of any conventional compacting technique, such as, for example: compaction by vibration, compaction by mechanical pressure, compaction by impacts and compaction by a combination of impacts and vibrations.

In the present invention, step c) of infiltrating the porous preform of step b) with a liquid precursor of the structural matrix is performed by means of any conventional infiltration technique, such as, for example: gas pressure infiltration, microwave-assisted infiltration, centrifugal infiltration and mechanical pressure infiltration (squeeze casting).

In the present invention, step e) of removing the sacrificial material from the one or more guest phases is performed by means of a process of the state of the art which is suitable depending on the nature thereof, for example: dissolution in liquid phases, one of the most common being water and aqueous solutions (for example, in coatings with high solubility in aqueous solutions such as NaCl), controlled thermal decomposition (for example, if the coating is a saline carbonate), and controlled combustion (for example, if the coating is made of carbon or is polymeric).

In a particular embodiment, the method of the present invention comprises an additional step of mixing particles of sacrificial material together with particles of the one or more guest phases coated in step a) in order to be compacted in step b). When this additional step is performed, the final foam material obtained comprises some of the pores thereof which are free of one or more guest phases and completely occupied by fluid.

In a particular embodiment, the method of the present invention comprises an additional step, before or after step e) of removing the sacrificial material from the one or more guest phases, wherein the precursor phase of the structural matrix is subjected to suitable treatment.

In a third aspect, the present invention relates to the use of the foam material of the present invention for the adsorption of gases, liquids or dissolved solids.

In a fourth aspect, the present invention relates to the use of the foam material of the present invention as a catalyst.

In another aspect, the present invention relates to the use of the foam material of the present invention as a filter for inorganic or biological substances.

In another aspect, the present invention relates to the use of the foam material of the present invention for releasing chemical or pharmaceutical substances.

In another aspect, the present invention relates to the use of the foam material of the present invention as material for an implant. In particular, the foam material of the present invention acts as an implant enabling the growth of living tissue therein with one or more adsorbent guest phases, such that it retains at least one substance with pharmacological activity in a living organism, such that said substance is released in a controlled manner by desorption from the guest phases in the living organism.

In another aspect, the present invention relates to the use of the foam material of the present invention as magnetic material. In particular, the foam material of the present invention contains one or several guest phases with magnetic properties and acts as a material which can be magnetically adhered to equipment having magnets or electrically-generated magnetic fields (electronic equipment) and enables the cooling thereof by means of a heat-transferring fluid.

In another aspect, the present invention relates to the use of the foam material of the present invention as impact-absorbing material. In particular, the foam material of the present invention acts as impact-absorbing material in parts for passive security in ground, air and aquatic transportation vehicles.

In another aspect, the present invention relates to the use of the foam material of the present invention as electrode material. In particular, the foam material of the present invention acts as an electrode for the electrochemical conversion in processes for chemical synthesis or decontamination of water and/or air.

In another aspect, the present invention relates to the use of the foam material of the present invention as material for absorbing electromagnetic radiation. In particular, the foam material of the present invention acts as an absorber of electromagnetic radiation for the transformation thereof into heat. In another particular use, the foam material of the present invention acts as material for absorbing electromagnetic radiation for the transformation thereof into electrical energy.

In another aspect, the present invention relates to the use of the foam material of the present invention as material for resonating radar waves, applied in radar invisibility technologies. In particular, the foam material of the present invention can be made up of a structural matrix and one or several dielectric guest phases, and a fluid made up of a liquid metal at the application temperature, such that the foam material configures a large assembly of electrical inductors and capacitors which, together, create a resonating effect which can trap and suppress radar waves at certain frequencies.

In another aspect, the present invention relates to the use of the foam material of the present invention as a template material for crystalline growth. In particular, the foam material of the present invention acts as a template which enables the crystalline growth in the gap existing between the structural matrix and the one or more guest phases.

The foam material of the present invention has the advantages commented below.

i) The structural matrix of the foam material of the present invention fulfils its funtionality in an independent manner (for example, as a structural material, thermally conductive material, electrically conductive material, etc.).

ii) The one or more guest phases of the foam material of the present invention fulfils its funtionality in an independent manner. The surface area of the one or more guest phases is completely accessible by the fluid, such that the entirety of the surface and of the volume of the one or more guest phases is perfectly functional inside the pores of the foam.

BRIEF DESCRIPTION OF THE SEVERAL VIEWS OF THE DRAWINGS

FIG. 4 shows a diagram of equipment for the coating of finely divided material in the form of particles with NaCl, which was used in the development of the exemplary embodiments presented in the present invention. The equipment consists of a quartz tube (9) having two inlet holes, one (10) for pressurised air—which maintains the particles (11) in suspension forming a fluidised bed—and another (12) for a nebulised NaCl solution. The equipment has a porous filter (13), which does not allow the particles to escape through the lower portion of the tube, and is heated by means of electrical resistances (14).

FIGS. 5(a), 5(b), 5(c), and 5(d) show images of a foam material obtained starting from a metal structural matrix (1), specifically aluminium, the guest phase (2) of which are SiC particles which fill the entirety of the pores, (a), (b) and (c) are images obtained by a scanning electron microscope (SEM) and (d) is an image obtained by conventional photography. Image (a) shows the angular morphology of the SiC particles, with an average diameter of 750 micrometres; image (b) shows these same particles with a sodium chloride (NaCl) coating, as a sacrificial material (4), with a thickness in the interval of 20-50 micrometres achieved with the device of FIG. 4; image (c) shows an image of two SiC particles as a guest phase in the cavities of the aluminium structural matrix; image (d) shows a photograph of a part made of the material.

DESCRIPTION OF SPECIFIC EMBODIMENTS OF THE INVENTION

Figures 1A, 1B:
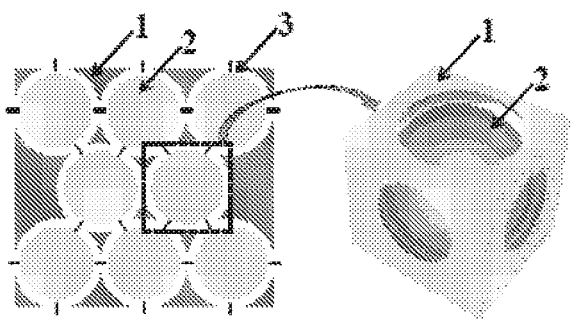
FIGs. 1(a) and 1(b) showsa diagram showing the interconnection of pores existing in a foam material with structural matrix (1) and with guest phase (2) and the manner wherein a guest particle (2) is accommodated in a pore (3) of the foam material: (a) drawing in two dimensions wherein the lines represent interconnecting openings between pores; and (b) three-dimensional representation of a representative fraction volume containing a guest particle (2) accommodated in a pore (3).

The foam material of the present invention is configured, in the simplest embodiment thereof, by three phases (see FIG. 1):
- a structural matrix (1), comprising a plurality of interconnected pores (3),
- a guest phase (2), in the finely divided form of particles or fibres, which is accommodated in the entirety or in a portion of the pores, and
- a fluid, the nature of which depends on the environment wherein the material is located, since the pores (3) are connected to the outside through the interconnections between them.

As mentioned in the general description of the invention, the foam material of the present invention can be made up of several guest phases (2 and 2") with different natures, so that each of them provides a different functionality to the final foam material.

The material making up the guest phase (2) is preferably selected in a finely divided state, in the form of particles or fibres, the dimensions of which can vary in the interval of 0.1 micrometres-1 centimetre in diameter for particles and in the same interval in diameter and in the interval of 0.1 micrometres-5 centimetres long for fibres.

Figures 2A, 2B, 2C:
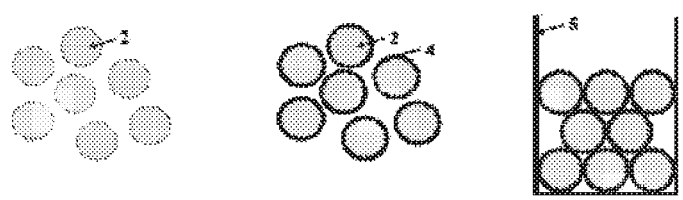
FIG. 2 illustrates the manufacturing process of a foam material with a guest phase filling 100% of the cavities. The fundamental steps are as follows:
A. Manufacture of the preform
  (a) guest phase (2) in the finely divided form of particles or fibres;
  (b) coating of the guest phase (2) with a sacrificial material (4);
  (c) compaction of the coated guest phase (2) until it forms a porous preform accommodated in moulds (5) suitable for the infiltration;
B. Infiltration
  (d) infiltration of the porous preform with a liquid precursor (1') of the foam material,
  (e) directional solidification of the liquid precursor (1') of the foam material by means of a cooling system (6) which enables directional cooling;
  (f) machining of the structural matrix (1) with conventional tools (7) and techniques;
C. Processing of the foam material
  (g) removal of the sacrificial material (4) either by dissolution (g1) in a liquid phase (8) or by controlled reaction (g2) with a liquid or gas phase (8') until a foam with interconnected pores (h) with guest phases (2) completely filling the cavities thereof is obtained.
Figures 2D, 2E, 2F:
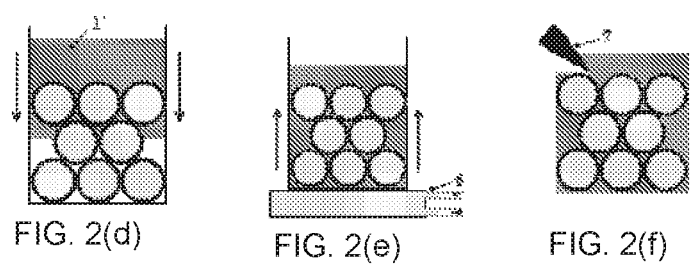
Figures 2G, 2H, 2I:
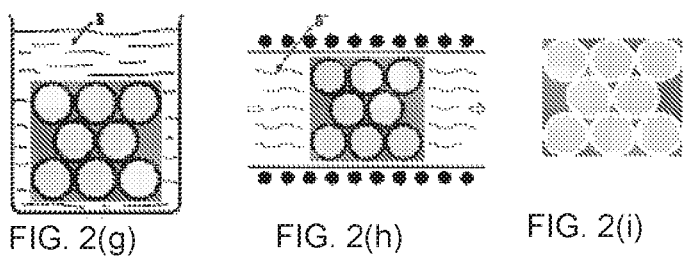

In the simplest embodiment thereof, the method for manufacturing the foam material with at least one guest phase (2) and at least one sacrificial material (4) comprises the following steps (see FIG. 2, FIG. 3 and FIG. 4 for greater detail):

a) continuous coating of the guest phase (2) previously divided into particles or fibres, with at least one sacrificial material (4), b) compaction of the coated guest phase (2) obtained in step a) until a porous preform is formed, c) infiltration of the porous preform of step b), with a liquid precursor of the structural matrix (1), d) solidification of the liquid precursor (1') of step c) and machining e) removal of the sacrificial material (4) from the guest phase.

The coating of the guest phase (2) is done with a sacrificial material (4) the nature of which is selected depending on the infiltrating liquid, since the melting/softening point thereof must be higher than that of the other. The sacrificial material (4) is preferably selected from among: saline halides (i.e. NaCl, KCl), saline carbonates (i.e. $K_2CO_3$, $CaCO_3$), strontium fluorides ($SrF_2$) or barium ($BaF_2$), sodium aluminate ($NaAlO_2$), saline sulphates (i.e. $MgSO_4$) and silicon oxide ($SiO_2$).

The coating of the guest phase (2) with the coating material (4) can have a thickness preferably selected in the interval of 1 micrometre-5 millimetres.

The coating of the guest phase (2) must be continuous. A continuous coating generates foam materials wherein the guest phase (2) and the structural matrix (1) do not maintain any bond.

The guest phase (2) coated with the sacrificial material (4) is compacted in crucibles (5), the nature of which depends on the melting/softening point and the chemical compatibility with the liquid with which the infiltration step will be performed. The nature of the crucible (5) is preferably selected among the following group: glass (for liquids compatible with a melting/softening point less than 400° C.), pyrex glass (for liquids compatible with a melting/softening point less than 600° C.), quartz (for liquids compatible with a melting/softening point less than 1500° C.), alumina (for liquids compatible with a melting/softening point less than 2000° C.), graphite (for liquids compatible with a melting/softening point less than 3500° C.). The compaction of the guest phase (2) coated with the sacrificial material (4) is performed by means of a conventional compaction technique, preferably selected from among the following: compaction by vibration, compaction by mechanical pressure, compaction by impacts or compaction by a combination of impacts and vibrations.

The porous preform generated is subsequently infiltrated with a liquid precursor of the solid phase (1') which will form the structural matrix of the foam material. The infiltration can be preferably achieved by gas pressure infiltration, microwave-assisted infiltration, centrifugal infiltration or mechanical pressure (squeeze casting). Subsequent to the infiltration, the directional solidification of the liquid infiltrating material is then performed. Then, the demoulding of the material and the machining thereof with conventional tools and techniques (7) are then performed. It is possible that certain precursor materials (1') may need to be suitably treated to modify the structure thereof (for example, graphite precursors such as mesophase pitch can be thermally treated until graphite material is generated). These treatments can be performed before or after the step of removing the sacrificial material (4) coating the guest phase (2).

The coating material (4) is removed by following different methodologies depending on the nature thereof. The removal method can be based on dissolution in a liquid phase (8) or on a controlled reaction with a liquid or gas phase (8'), preferably selected from among the following group:

a) removal by dissolution in water or aqueous solutions—preferably for alkaline halides (i.e. NaCl, KCl), alkaline and alkaline earth carbonates (i.e. $K_2CO_3$, $CaCO_3$), strontium fluoride ($SrF_2$), barium fluoride ($BaF_2$), sodium aluminate ($NaAlO_2$), magnesium sulphate ($MgSO_4$);

b) removal by dissolution in acids—preferably for silicon oxide ($SiO_2$);

c) removal by thermal treatment—preferably for alkaline and alkaline earth carbonates (i.e. $K_2CO_3$, $CaCO_3$);

d) combustion (thermal treatment in an atmosphere with oxygen present)—preferably for coatings made of carbon or polymers.

The processes based on removing the sacrificial material (4) by dissolution can be preferably carried out by means of the following methods: i) immersion in the solution for a controlled time; ii) immersion in the solution for a controlled time followed by injection of the solution at a certain pressure for a controlled time. This combined method (ii) enables a quicker removal of the sacrificial material (4).

The dimension of the free space between the cavities of the structural matrix (1) and the guest phase (2) is defined by the thickness of the coating material (4).

The interconnection opening between the different pores of the foam material depends on the shape adopted by the particles or fibres of the guest phase (2) after the coating thereof with the sacrificial material (4) and the manner wherein these touch each other in the compacted bed which forms the porous preform. In any case, it must be ensured that the interconnection opening diameter is not the same or larger than the diameter of the particles or fibres of the guest phase (2), since this could cause the outlet of the guest phase (2) from the material and the loss of the functionality of the material, which would transform into a conventional foam of the material which forms the structural matrix (1).

Figures 3A, 3B, 3C, 3D:
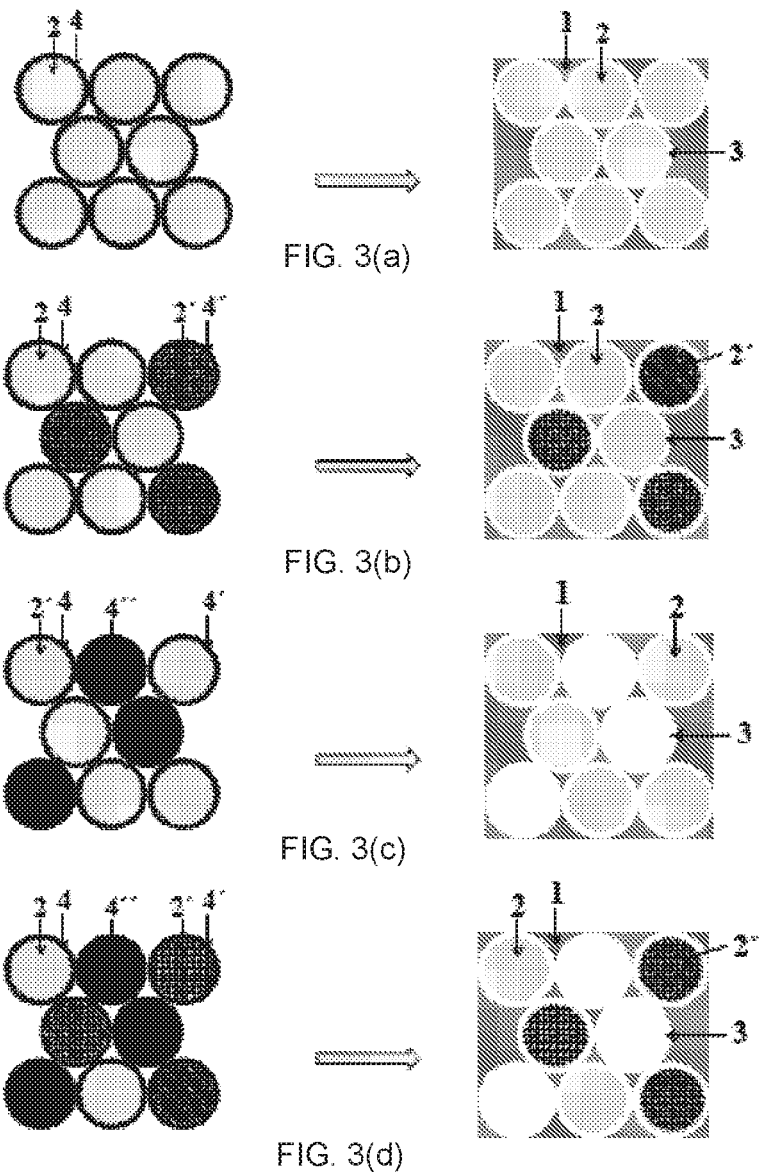
FIG. 3 illustrates different types of foam materials with guest phases which can be achieved depending on the type of porous preform started with. The porous preforms are shown on the left and the different types of foam materials obtained therefrom are shown on the right:
  a) Porous preform obtained by compaction of a single guest phase (2) coated by a single sacrificial material (4), in order to give rise to a foam material comprising all the pores occupied by the guest phase (2).
  b) Porous preform obtained by compaction of more than one guest phase (2 and 2'), and coated with more than one sacrificial material (4 and 4') in order to give rise to a foam material comprising all the pores occupied by the guest phases (2 and 2').
  c) Porous preform obtained by compaction of a guest phase (2) coated with more than one sacrificial material (4 and 4'), together with sacrificial material particles (4") in order to give rise to a foam material comprising only some of the pores occupied by the guest phase (2).
  d) Porous preform obtained by compaction of more than one guest phase (2 and 2') coated with by-more than one sacrificial material (4 and 4') together with particles of sacrificial material (4") in order to give rise to a foam material comprising some of the pores occupied by the guest phases (2 and 2').
Figure 6A:
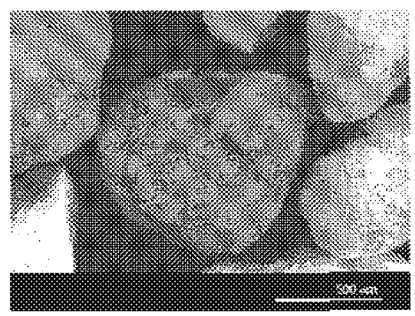
FIG. 6 shows images of a foam material obtained starting from a ceramic structural matrix (1), specifically mesophase pitch, the guest phase (2) of which are activated carbon particles which partially fill the pores of the foam material. (a), (b) and (c) are images obtained by a scanning electron microscope (SEM) and (d) is an image obtained by conventional photography. Image (a) shows the morphology of the active carbon particles, with an average diameter of 1 millimetre; image (b) shows these same particles with a sodium chloride (NaCl) coating with a thickness in the interval of 70-100 micrometres achieved with the device of FIG. 4; image (c) shows an image of an activated carbon particle as a guest phase (2) in a pore of the foam material made of mesophase pitch; image (d) shows a photograph of a part made of the material.
Figure 6B:
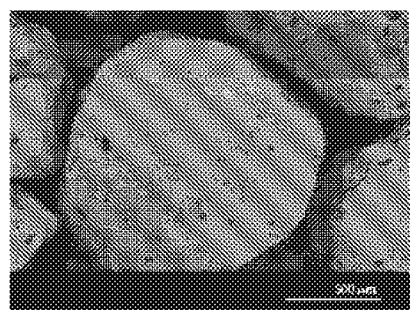
Figure 6C:
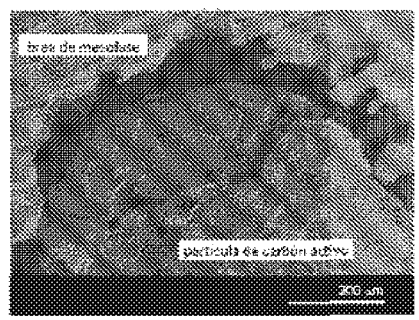
Figure 6D:
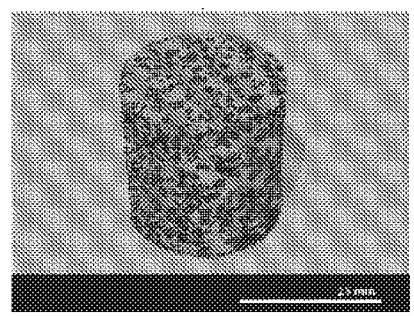
Figure 7A:
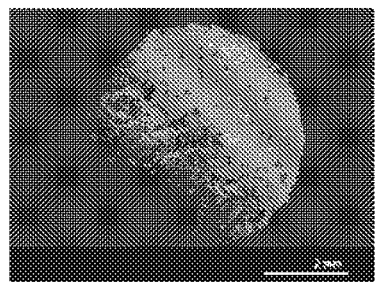
FIG. 7 shows images of a foam material obtained starting from a metal structural matrix (1), specifically tin, the guest phase (2) of which are spherical cobalt particles which partially fill the pores, (a) is an image obtained by a scanning electron microscopy (SEM) and (b), (c) and (d) are images obtained by optical microscope. Image (a) shows a cobalt particle, with an average diameter of 5 millimetres, coated with sodium chloride (NaCl), as a sacrificial material (4), with a thickness in the interval of 150-200 micrometres achieved with the device of FIG. 4; images (b), (c) and (d) show images of cobalt particles as a guest phase (2) in the pores of the foam material made of tin.
Figure 7B:
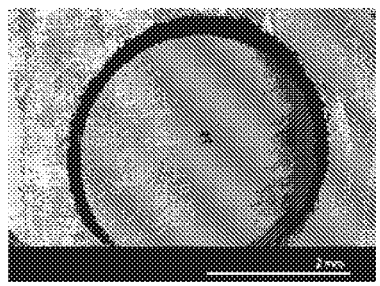
Figure 7C:
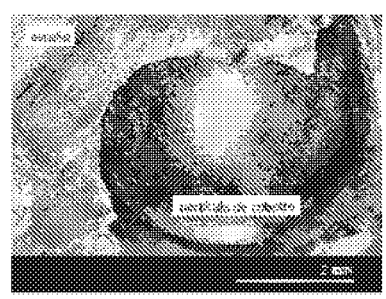
Figure 7D:
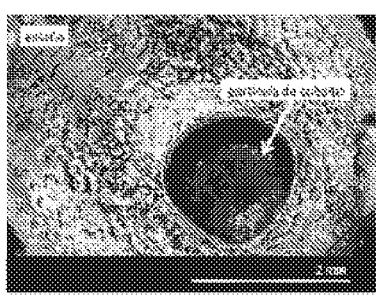

As shown in FIG. 3, the foam material can contain more than one guest phase (2, 2') and can be made with one or several sacrificial coating materials (4, 4'), apart from containing cavities not occupied by a guest phase (2) generated starting from sacrificial particles (4") with the same or different nature as the sacrificial material or materials used to coat the one or more guest phases.

Exemplary Embodiments

EXAMPLE 1

This example describes the embodiment of foam material made of aluminium with pores interconnected and with guest phase (2) of silicon carbide (SiC) particles with an average diameter of 750 micrometres which fill up the entirety (100%) of the pores. The particles of the guest phase (2) were coated with NaCl as the sacrificial material (4), by means of the deposition method using forced spray precipitation. To do so, the device shown in FIG. 4 was prepared, which enables the particles to be maintained in suspension by means of a fluidised bed generated by the inlet of an inert gas (argon) through a porous material placed in the lower portion of the device. The system enables the particles to be heated to a maximum temperature of 1000° C. Specifically, the SiC particles were maintained at a temperature of 300° C. Through the inlet hole ((12) in FIG. 4) a mist generated by the vaporisation of a solution prepared with 20 g of NaCl in 100 g of water was allowed to enter. The mist was projected during 5 second intervals, with resting intervals between each misting of 30 seconds. By means of this method, a compact layer of NaCl with a coating thickness of 20-50 micrometres was achieved.

18 grams of SiC particles thereby coated (SiC—NaCl) were compacted in a crucible made of quartz with a diameter of 17 mm and a length of 150 mm. The compacted bed reached a height of 50 mm inside the tube. A part made of aluminium metal (25 g) was added in the upper portion of the bed and the assembly was transferred to the inside of an infiltration chamber. This was closed and a vacuum was applied at a pressure of 0.1 mbar. Then the temperature was raised to 750° C. by means of a heating rate of 3° C./min. The temperature was maintained at 750° C. for 15 min and then 5 bar of pressure were applied in the chamber.

The pressure was maintained for 2 minutes and immediately afterwards, the crucible was lowered to the bottom of the infiltration chamber, which acts as a cold trap for quick and directional solidification. After the solidification, the sample was demoulded and machined in order to remove the excess metal, until the coated particles were able to be accessed on all the faces of the cylinder. The machining was performed by means of a cutting saw and then by means of a lathe, using cutting tools, in order to finally perform a fine finish by means of successive abrasive sheets of sandpaper with grits of 240 and 400. The removal of the sacrificial material (4) was achieved by means of immersion of the part in water in a glass of precipitates, magnetically stirred for 5 minutes. After this time, the part was fitted to a tube through which water was passed at a pressure of 4 bar, with which the complete dissolution of the salt was achieved in a time of 15 minutes. Details of the final material can be seen in FIG. 5.

EXAMPLE 2

This example describes the embodiment of a foam material made of aluminium with pores interconnected and with guest phase (2) of silicon carbide (SiC) particles with an average diameter of 750 micrometres which fill up half (50%) of the pores. The embodiment is identical to that of EXAMPLE 1 but starting from a mixture of SiC particles with an average diameter of 750 micrometres coated with NaCl (SiC—NaCl) with a coating thickness of 20-50 micrometres and NaCl particles with an average diameter of 750 micrometres. The volume ratio of the mixture used is 1:1 for SiC—NaCl: NaCl, for which 8.88 grams of SiC—NaCl particles and 6.47 grams of NaCl particles are used.

EXAMPLE 3

This example describes the embodiment of foam material made of mesophase pitch with pores interconnected and with guest phase (2) of activated carbon particles with an average diameter of 1 millimetre which fill up the entirety (100%) of the pores. The particles were coated with NaCl by means of the deposition method using forced spray precipitation in the same manner as in EXAMPLE 1. A coating thickness of 70-100 micrometres was achieved. The infiltration with mesophase pitch was performed at 400° C. by means of an infiltration process identical to the one described in EXAMPLE 1. The embodiment is identical to that of EXAMPLE 1 but starting with an amount of 13 grams of active carbon particles. Details of the final material can be seen in FIG. 6.

EXAMPLE 4

This example describes the embodiment of foam material made of tin with pores interconnected and with guest phase (2) of spherical cobalt particles with an average diameter of 5 millimetres which fill up half (50%) of the pores. The particles were coated with NaCl by means of the deposition method using forced spray precipitation in the same manner as in EXAMPLE 1. A coating thickness of 150-200 micrometres was achieved. The infiltration with tin was performed at 400° C. by means of an infiltration process identical to the one described in EXAMPLE 1. The embodiment is identical to that of EXAMPLE 1 but starting from a mixture of cobalt particles with an average diameter of 5 millimetres coated with NaCl (Co—NaCl) and NaCl particles with an average diameter of 3 millimetres. The volume ratio of the mixture used is 1:1 for Co—NaCl: NaCl, for which 23 grams of Co—NaCl particles and 6.5 grams of NaCl particles were used. Details of the end material can be seen in FIG. 7.

EXAMPLE 5

This example describes the embodiment of foam material made of tin with pores interconnected and with two guest phases of activated carbon particles (2) and spherical cobalt particles (2″) with average diameters of 1 millimetre and 5 millimetres, respectively. The guest phase (2) of activated carbon particles fill 25% of the cavities of the foam and the guest phase of cobalt particles (2′) fill another 25% of the pores. The particles were coated with NaCl by means of the deposition method using forced spray precipitation in the same manner as in EXAMPLE 1. A coating thickness of 70-100 micrometres was achieved in the activated carbon particles and 150-200 micrometres in the cobalt particles. The embodiment is identical to that of EXAMPLE 4 but starting from a mixture of particles in a volume ratio of 1:1:2 for carbon-NaCl:Co—NaCl:NaCl, for which 3.27 g of activated carbon particles, 11.48 g of cobalt particles and 6.47 g of NaCl particles were used.

What is claimed us:

1. A foam material comprising:
    a structural matrix,
    one or more guest phases made of a functional material in the form of a particle or a fiber wherein the particles or fibers are stacked one on top of each other and interstitial spaces between the particles or fibers filled with the structural matrix, and
    a fluid,
    wherein:
    the structural matrix is made up of a metal selected from the group consisting of tin, aluminum, copper, titanium, mixture and metal alloys thereof, and comprises a plurality of interconnected pores wherein the pores are in fluid communication with each other by an interconnection opening having a diameter that is not the same or larger than a diameter of the particle or fiber of the one or more guest phases, and wherein a wall of the pore has a shape matching and conforming to a shape of the particle or the fiber, the one or more guest phases are accommodated inside at least one pore of the structural matrix without maintaining any bond with said structural matrix such that between the wall of the pore of the foam material and the surface of the guest phase there is a gauge of space that is occupied by the fluid, and the fluid is accommodated inside the pores and surrounds the entirety of the one or more guest phases in the pore.

2. The foam material according to claim 1, wherein the functional material is selected from the group consisting of an adsorbent material, an absorbent (impacts or radiation) material, a catalytic material, a magnetic material, a supporting or a catalyst-supporting material for releasing chemical and/or pharmaceutical substances, and a material with an electrode function.

3. The foam material according to claim 1, wherein the functional material is selected from the group consisting of: carbon, active carbon, graphite, alumina ($Al_2O_3$), activated alumina ($Al_2O_3$), silicon (Si), silicon carbide (SiC), activated SiC, titanium carbide (TiC), activated TiC, aluminium nitride (AlN), cerium oxide ($CeO_2$), activated $CeO_2$, titania ($TiO_2$), activated $TiO_2$, zeolites, metal-organic frameworks (MOFs), platinum (Pt), rhodium (Rh), palladium (Pd), iron, cobalt, nickel and metal alloys thereof, iron oxides ($Fe_xO_y$), cobalt oxides ($Co_xO_y$), and nickel oxides ($Ni_xO_y$).

4. The foam material according to claim 1, wherein the fluid is a liquid or a gas.

5. A method for preparing a foam material according to claim 1, comprising the following steps:
    a) coating a continuous layer of at least one sacrificial particulate material on the one or more guest phases made of a functional material in the form of a particle or a fiber,
    b) compacting the one or more coated guest phases until a porous preform is formed such that the particles or the fibers are stacked one on top of each other and interstitial spaces formed between the particles or the fibers,
    c) infiltrating the porous preform, with a precursor liquid of the structural matrix,
    d) solidifying the precursor liquid and machining,
    e) removing the at least one sacrificial particulate material from the one or more coated guest phases.

6. The method according to claim 5, wherein the at least one sacrificial particulate material is a salt selected from the group consisting of halides, carbonates, fluorides, aluminates, sulphates and silicates.

7. The method according to claim 5, comprising an additional step of compacting the at least one sacrificial particulate material and the one or more coated guest phases.

8. The method according to claim 5, wherein the coating step is performed with two or more sacrificial particulate materials.

* * * * *